US008285372B2

(12) United States Patent
Sing

(10) Patent No.: US 8,285,372 B2
(45) Date of Patent: Oct. 9, 2012

(54) ALERTNESS/DROWSINESS AND COGNITIVE CAPACITY INDEX

(75) Inventor: Helen C. Sing, Takoma Park, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 894 days.

(21) Appl. No.: 12/339,864

(22) Filed: Dec. 19, 2008

(65) Prior Publication Data

US 2009/0149770 A1    Jun. 11, 2009

Related U.S. Application Data

(63) Continuation-in-part of application No. PCT/US2007/014541, filed on Jun. 22, 2007.

(60) Provisional application No. 60/823,172, filed on Aug. 22, 2006, provisional application No. 60/815,565, filed on Jun. 22, 2006.

(51) Int. Cl.
*A61B 5/04* (2006.01)

(52) U.S. Cl. ........................................................ 600/544
(58) Field of Classification Search .................. 600/544, 600/545
See application file for complete search history.

(56) References Cited

U.S. PATENT DOCUMENTS

| 5,230,346 | A |   | 7/1993  | Leuchter et al. |
|-----------|---|---|---------|-----------------|
| 5,259,390 | A |   | 11/1993 | MacLean |
| 5,320,109 | A |   | 6/1994  | Chamoun et al. |
| 5,433,223 | A |   | 7/1995  | Moore-Ede et al. |
| 5,566,067 | A |   | 10/1996 | Hobson et al. |
| 5,568,127 | A |   | 10/1996 | Bang |
| 5,570,698 | A |   | 11/1996 | Liang |
| 5,585,785 | A |   | 12/1996 | Gwin |
| 5,595,488 | A |   | 1/1997  | Gozlan |
| 5,647,633 | A |   | 7/1997  | Fukuoka |
| 5,682,144 | A |   | 10/1997 | Mannik |
| 5,689,241 | A |   | 11/1997 | Clarke, Sr. et al. |
| 5,691,693 | A |   | 11/1997 | Kithil |
| 5,813,993 | A | * | 9/1998  | Kaplan et al. ............... 600/544 |
| 2001/0056225 | A1 | * | 12/2001 | DeVito ...................... 600/300 |
| 2002/0183644 | A1 | * | 12/2002 | Levendowski et al. ....... 600/544 |

OTHER PUBLICATIONS

Sing, et al. "High Freuqnecy EEG as a Measure of Cognitive Function Capacity: A Preliminary Report." Aviation, Space, and Envirionmenal Medicine. vol. 76, No. 7, Section III, Jul. 2005.*
Kaplan, R.F. An Innovative EEG Based Approach to Drowsiness Detection. Department of Systems and Control Engineering. Case Western Reserve University.*
Kaplan, R.F. An Innovative EEG Based Approach to Drowsiness Detection. Department of Systems and Engineering. Case Western Reserve University. May 1996. pp. 1-242.*

(Continued)

*Primary Examiner* — Patricia Mallari
*Assistant Examiner* — Tiffany Weston
(74) *Attorney, Agent, or Firm* — Elizabeth Arwine

(57) ABSTRACT

The invention includes a method and system for providing an Index representing the alertness state of an individual based at least in part on EEG signals obtained from the individual. In at least one embodiment, the EEG signals are divided into frequency bands and a total amplitude of the power is determined. Based on the proportion of the high frequency band compared to the proportion of the low frequency band, an Index is determined that is indicative of an individual's ability to perform a cognitive task.

28 Claims, 15 Drawing Sheets

OTHER PUBLICATIONS

Anderer, Peter, et al., "An E-Health Solution for Automatic Sleep Classification according to Rechtschaffen and Kales: Validation Study of the Somnolyzer 24 × 7 Utilizing the Siesta Database," Neuropsychobiology, Apr. 18, 2005, pp. 115-133, vol. 51.

Braver, ER, et al. "Long Hours and Fatigue: A Survey of Tractor-Trailer Drives," Journal of Health Policy, 1992 Autumn, Abstract, vol. 13 (3).

Boot, Max, "The New America Way of War," Foreign Affairs, Jul./Aug. 2003, available at http://www.foreignaffairs.org/20030701faessay15404/max-boot/the-new-american-way-of-war.html.

Herridge, Catherine, "Pilot, 1st Officer Slept While Approaching Denver, Lawmakers Says," Fox News, Nov. 1, 2007, available at http://www.foxnews.com/story/0,2933,307019,00.html.

Rechtschaffen, Allan, et al., "A Manual of Standardized Terminology, Techniques and Scoring System for Sleep Stages of Human Subjects," U.S. Department of Health, Education, and Welfare, Public Health Service—National Institutes of Health , 1968 (reprinted 1971), pp. 1-58.

Sing, Helen C., et al., "High-Frequency EEG as Measure of Cognitive Function Capacity: A Preliminary Report," Aviation, Space, and Environmental Medicine, Jul. 2005, pp. C114-C135, vol. 76, No. 7, Section II.

"AASM Publishes New Scoring Manual," Sleep Review, Apr. 18, 2007, available at http://www.sleepreviewmag.com/sleep_report/2007-04-18_01.asp.

"Exclusive: Nuclear Plant Guards Asleep on the Job. Exelon to Terminate Deal with Security Firm also under Contract with Major Federal Agencies," WCBSTV.com, Sep. 25, 2007, available at http://wcbstv.com/politics/peach.bottom.nuclear.2.291442.html.

The Center for National Truck Statistics, "Truck and Bus Accident Factbook 1994," Oct. 1996, pp. 1-103.

* cited by examiner

ALERTNESS/DROWSINESS AND COGNITIVE CAPACITY INDEX

This patent application is a continuation-in-part application of PCT Application No. PCT/US2007/014541 filed on Jun. 22, 2007 and published in the English language on Dec. 27, 2007. PCT Application No. PCT/US2007/014541 claims the benefit of U.S. provisional patent application No. 60/815,565 filed on Jun. 22, 2006 and U.S. provisional patent application No. 60/823,172 filed on Aug. 22, 2006.

I. FIELD OF THE INVENTION

The invention relates to using EEG information to calculate an index score that is indicative of the ability of an individual to perform a cognitive task.

II. BACKGROUND OF THE INVENTION

Sleep deprivation is inevitable in the military environment where the battlefield situation often involves 24 hours or more of continuous operation. Maintaining a high level of alertness and cognitive performance under demands of constant readiness around the clock is not only individually difficult, but also impossible to assess without a means of direct monitoring. The U.S. Army has long been concerned about the potential for catastrophic outcomes as consequences of sleep deprivation which result in poor judgment and performance on the part of military personnel whose decision making ability is impaired. This concern has been realized in the immediate past with the capture of soldiers in Iraq who took a wrong turn on a road and found themselves in unknown enemy territory It was later revealed that the soldiers on this expedition had been without sleep for longer than 24 hours, were cognitively impaired and unaware that they had misread the map. Boot, M., *The new American way of war*, Foreign Affairs, July/August 2003.

Consequential incidents due to sleep deprivation and sleep restriction pertain not only to the military, but also to the public sector in areas of transportation, nuclear facilities, emergency support, and health care providers among the more immediate concerns. Many incidents or near accidents occurring in the public arena are not publicized especially those involving pilot fatigue. Congress is currently investigating why these incidents are not reported to the public and cites the case on Mar. 4, 2004, where both pilot and co-pilot flew three sequential "red eyes" between Denver and Baltimore with only one hour in between flights. During the last 45 minutes of the third flight as it was approaching Denver, both pilot and co-pilot were sound asleep and missed all calls from the air traffic controller while the plane was traveling at 590 mph instead of less than 290 mph. Fortunately, the pilot did suddenly awake to hear the air traffic controller's frantic calls and was able to follow his instructions resulting in a safe landing. Foxnews.com, *Pilot 1$^{st}$ Officer Slept While Approaching Denver, Lawmaker Says*, Oct. 31, 2007.

Even more alarming are the results from a 1992 survey of tractor trailer truckers which found that 19% of the truckers admitted to having fallen asleep at the wheel in the previous month. Braver, E R et al., *Long hours and fatigue: a survey of tractor-trailer drivers*, Journal of Public Health Policy, 1992, Vol. 13, No. 3, pp. 341-366. A report from the Center for National Truck Statistics in 1994 included the disturbing statistic that annually over 5,000 fatalities and 110,000 injuries resulting from motor vehicle accidents involve commercial trucks in the United States. Center for National Truck Statistics, *Truck and bus accident factbook* 1994, Federal Highway Administration Office of Motor Carriers, 1996 (Report no. UMTRI-96-40). Knipling estimated that the percentage of vehicle crashes in which fatigue was a factor could be as high as 56%. Knipling, R R et al., *Crashes and fatalities related to driver drowsiness/fatigue: research note*, National Highway Traffic Safety Administration, 1994. Although the Department of Transportation (DOT) regulates work hours permitted for truck drivers, pilots, airport controllers and railroad engineers, there is no routine checking for status of alertness (hence being well rested) just prior to start of duty or during duty hours.

A more recent example documented security guards in a Pennsylvania nuclear plant were regularly asleep on the job for periods exceeding one hour. This public exposure resulted in loss of employment and dismissal of the security company providing the staff, but offered no remedy as to how this could be prevented in the future. (Weinberger, 2007).

Brain electrical activity, commonly referred to as electroencephalogram (EEG), is the manifestation of neuronal communication which may be discerned and recorded at the surface of the scalp by electrode sensors and subsequently displayed, measured, and analyzed. Clinically, the EEG is used for detection of brain pathology such as tumors, epileptic seizures, and behavioral abnormalities such as narcolepsy and attention deficit hyperactive disorder (ADHD). The brain signals, collectively referred to as an electroencephalograph, are analyzed for their constituent frequencies (rhythmic oscillations) and/or selective characteristic wave shapes to detect deviations from normal. In the sleep research laboratory, the EEG is used not only for determination of sleep/wake states and for quantification of sleep amount during nighttime sleep but also to track sleepiness level during the course of sleep deprivation studies of normal, healthy individuals.

Polysomnography is the methodology for defining the awake and sleep states from observation of EEG signals over an extended time period. As its name implies, other physiological measures are recorded synchronously with the EEG to aid in differentiating the awake from the sleep state as well as marking the different stages of sleep. Multiple electrode sensors are attached to the scalp, face, and body of the individual under study to record both the neurophysiological (EEG) and basic physiological measures such as electrooculogram (EOG) for recording eye movements; submental electromyogram (EMG) from the chin for detecting muscle movement; and electrocardiogram (EKG) for heart rate. Although the EEG is the main determinant of sleep characteristics, the EOG and EMG aid in defining Rapid Eye Movement (REM) sleep more commonly known as the dream stage in which it is conjectured that memory consolidation occurs. REM is thus distinguished from non-Rapid Eye Movement (NREM) sleep which defines all other sleep stages. Rolling eye movements observed in the EOG are characteristic during REM simultaneously with muscle atonia as noted in the EMG. During night time sleep, the REM state alternates with non-REM sleep in ultradian cycles of approximately 90 minutes and increases in length as non-REM length decreases in the progression towards the end of the sleep period. The EKG provides continuous monitoring of heart rate not only to assure normal functioning, but also to confirm the deeper sleep stages when the reduced rate of heart beats indicates slowing of body functions.

Although the frequency realm of EEG is in cycles per second or Hertz (Hz) and several orders of magnitude higher than that of ultradian frequencies (i.e., cycles/24 hours), the same fundamental principles of rhythmic behavior apply. The EEG signal as visually observed in its entirety is a combination of all the frequencies selected for recording in the acquisition process. Overall circadian rhythmicity is observed in the oscillation of the frequencies and depending on the frequency band, the cyclic variation mimics the circadian or is out of phase by 180°. That is, the band of low frequencies peaks in the hours of sleep while the band of high frequencies peaks during the waking active period.

Sleep researchers have devised an EEG (or polysomnography (PSG)) scoring system, considered to be the "gold standard" for evaluating sleep depth according to specific frequencies and patterns of EEG waveforms as established by Rechtschaffen and Kales. Rechtschaffen, A. et al., *A manual of standardized terminology, techniques and scoring system for sleep stages of human subjects*, Public Health Service, U.S. Government Printing Office, 1968 (reprinted 1971). The system consists of 6 levels in which sleep is scored within a 20 second or 30 second standard epoch as: Wake; Stage 1; Stage 2; Stage 3; Stage 4; and REM. By conventional Rechtschaffen and Kales practice, the EEG during the awake state consists mainly of frequencies between 12-50 Hz and is known as beta frequency although it is sometimes subcategorized as gamma in the 30-40 Hz range. Stage 1 is considered light sleep and the EEG is defined by a mix of predominantly alpha (7-14 Hz) and some theta (5-7 Hz) frequencies. It is not difficult to be awakened at this stage. Stage 2 is deeper sleep dominated by theta, along with some alpha. This stage is characterized by intrusions of specific wave patterns described as K-complexes and spindles because they resemble these descriptions and appears to be the threshold to actual sleep whereas Stage 1 is more the transitional state between awake and sleep. Stages 3 and 4 are marked by delta (1-4 Hz) frequencies with Stage 3 showing all of these frequencies while Stage 4 have both greater percentage and higher amplitude of 1 Hz and 2 Hz frequencies. Stage 4 represents the deepest sleep stage where frequency of neuronal communication is lowest and judging from the high amplitude of these lowest frequencies, indicative that the sum of active brain function is essentially minimal throughout the brain, i.e., the brain has essentially "shut down". Arousal from this sleep stage is extremely difficult.

Sleep scorers mark latency to sleep with the appearance of K-complexes or sleep spindles seen in Stage 1 or 2. Latency of 5 minutes or less is considered pathological in the clinical setting under normal conditions, but in the sleep research laboratory, this is quite often the case in sleep restricted or sleep deprived individuals with no existing pathology.

It is to be noted that EEG records are usually visually scanned and manually Scored—a long, tedious process with emphasis of the process on either the sleep or awake state and little or no attention directed to the between state of drowsiness. There has been little change in manual EEG sleep stage scoring for over 35 years, until recently where attempts have been made to automate the procedure with some measure of accuracy by following the Rechtschaffen and Kales guidelines as well as the more recent American Association of Sleep Medicine's *The AASM Manual for the Scoring of Sleep and Associated Events*. Anderer, P., *An E-health solution for automatic sleep classification according to Rechtschaffen and Kales validation study of the Sommolyzer 24×7 utilizing the Siesta database*, Neuropsychobiology, 2005, Vol. 51, No. 3, pp. 115-123.

Most commercial EEG systems are designed to record up to about 256 Hz, because that is the upper limit for extracting useful information in PSG scoring. As a result, there has been no need to examine EEG data for the frequencies above 256 Hz.

There is a general emphasis in making polysomnographic determinations of whether a person is either sleep or awake with little attention directed to the in between states of drowsiness or alertness. Existing alertness systems are looking for physical manifestations indicating that a person is alert or not alert. Methods and apparatuses related to alertness detection fall into five basic categories: a method/apparatus for unobtrusively monitoring current alertness level; a method/apparatus for unobtrusively monitoring current alertness level and providing a warning/alarm to the user of decreased alertness and/or to increase user's alertness level; a method/apparatus for monitoring current alertness level based on the user's responses to some secondary task possibly with an alarm device to warn the user of decreased alertness and/or to increase user's alertness level; methods to increase alertness; and a method/apparatus for predicting past, current, or future alertness.

These methods and apparatuses that unobtrusively monitor the current alertness level are based on an "embedded measures" approach. That is, such methods infer alertness/drowsiness from the current level of some factor (e.g., eye position or closure) assumed to correlate with alertness/drowsiness. Issued patents of this type include U.S. Pat. No. 5,689,241 to J. Clarke, Sr., et al. disclosing an apparatus to detect eye closure and ambient temperature around the nose and mouth; U.S. Pat. No. 5,682,144 to K. Mannik disclosing an apparatus to detect eye closure; and U.S. Pat. No. 5,570, 698 to C. Liang et al. disclosing an apparatus to monitor eye localization and motion to detect sleepiness. An obvious disadvantage of these types of methods and apparatuses is that the measures are likely detecting sleep onset itself rather than small decreases in alertness.

In some patents, methods for embedded monitoring of alertness/drowsiness are combined with additional methods for signaling the user of decreased alertness and/or increasing alertness. Issued patents of this type include U.S. Pat. No. 5,691,693 to P. Kithil describing a device that senses a vehicle operator's head position and motion to compare current data to profiles of "normal" head motion and "impaired" head motion. Warning devices are activated when head motion deviates from the "normal" in some predetermined way. U.S. Pat. No. 5,585,785 to R. Gwin et al. describes an apparatus and a method for measuring total handgrip pressure on a steering wheel such that an alarm is sounded when the grip pressure falls below a predetermined "lower limit" indicating drowsiness. U.S. Pat. No. 5,568,127 to H. Bang describes a device for detecting drowsiness as indicated by the user's chin contacting an alarm device, which then produces a tactile and auditory warning. U.S. Pat. No. 5,566,067 to J. Hobson et al. describes a method and an apparatus to detect eyelid movements. A change in detected eyelid movements from a predetermined threshold causes an output signal/alarm (preferably auditory). As with the first category of methods and apparatuses, a disadvantage here is that the measures are likely detecting sleep onset itself rather than small decreases in alertness.

Other alertness/drowsiness monitoring devices have been developed based on a "primary/secondary task" approach. For example, U.S. Pat. No. 5,595,488 to E. Gozlan et al. describes an apparatus and a method for presenting auditory, visual, or tactile stimuli to an individual to which the individual must respond (secondary task) while performing the primary task of interest (e.g., driving). Responses on the secondary task are compared to baseline "alert" levels for responding. U.S. Pat. No. 5,259,390 to A. MacLean describes a device in which the user responds to a relatively innocuous vibrating stimulus. The speed to respond to the stimulus is used as a measure of the alertness level. A disadvantage here is that the apparatus requires responses to a secondary task to infer alertness, thereby altering and possibly interfering with the primary task.

Other methods exist solely for increasing alertness and depend upon the user to self-evaluate alertness level and activate the device when the user feels drowsy. An example of the latter is U.S. Pat. No. 5,647,633 and related patents to M. Fukuoka in which a method/apparatus is described for causing the user's seat to vibrate when the user detects drowsiness. Obvious disadvantages of such devices are that the user must be able to accurately self-assess his/her current level of alertness, and that the user must be able to correctly act upon this assessment.

Methods also exist to predict alertness level based on user inputs known empirically to modify alertness. U.S. Pat. No. 5,433,223 to M. Moore-Ede et al. describes a method for predicting the likely alertness level of an individual at a specific point in time (past, current or future) based upon a mathematical computation of a variety of factors (referred to as "real-world" factors) that bear some relationship to alterations in alertness. The individual's Baseline Alertness Curve (BAC) is first determined based on five inputs and represents the optimal alertness curve displayed in a stable environment. Next, the BAC is modified by alertness modifying stimuli to arrive at a Modified Baseline Alertness Curve. Thus, the method is a means for predicting an individual's alertness level, not cognitive performance.

More recently a method was developed that uses information in an EEG signal in frequency bands above 30 Hz, for example, 80-420 Hz. U.S. Pat. No. 5,813,993 to Kaplan et al. describes such a method that uses a weighted sum of the inverse of the energy of a subject's EEG signal in selected frequency bands. The energy level for each frequency band is inverted and then weighted prior to the inverted energy levels being summed together to provide a score reflective of the subject's alertness or drowsiness.

III. SUMMARY OF THE INVENTION

The detection of drowsiness in individuals tasked with maintaining a high level of alertness in critical work situations would be highly desirable in preventing accidents by signaling a warning of incipient sleep. It would be invaluable in a variety of environments where drowsiness leading to sleep may result in catastrophic failure such as in the transportation field or on the battlefield. For example, if military personnel can be monitored for continuous assessment of their alertness/drowsiness state and this information transmitted to field commanders, timely intervention and sleep discipline may be imposed as needed.

The invention includes a method and system for providing an Index representing the alertness state of an individual based at least in part on EEG signals obtained from the individual. In at least one embodiment, the EEG signals are divided into frequency bands and a total amplitude (square root of the power) is determined. Based on the proportion of the high frequency band compared to the proportion of the low frequency band, an Index is determined that is indicative of an individual's ability to perform a cognitive task.

The invention in at least one embodiment includes a system including means for transforming a EEG signal to the frequency domain with a Discrete Fourier Transform, means for obtaining the amplitude of each frequency component, means for summing all of the amplitudes of each frequency component to obtain a total amplitude, means for summing all of the amplitudes of frequencies in the range of 201-500 Hz to obtain a high frequency amplitude, means for summing all of the amplitudes of frequencies in the range of 1 to at least 15 Hz to obtain a low frequency amplitude, and means for calculating an Index based on the total amplitude, the high frequency amplitude, and the low frequency amplitude.

The invention in at least one embodiment includes a computer program product for providing an Index, the program product having a computer readable medium; first program instruction means for transforming a digital EEG signal to the frequency domain with a Discrete Fourier Transform, second program instruction means for obtaining the amplitude of each frequency component, third program instruction means for summing all of the amplitudes of each frequency component to obtain a total amplitude, fourth program instruction means for summing all of the amplitudes of frequencies in the range of 201-500 Hz to obtain a high frequency amplitude, fifth program instruction means for summing all of the amplitudes of frequencies in the range of 1 to at least 15 Hz to obtain a low frequency amplitude, and sixth program instruction means for calculating an Index based on the total amplitude, the high frequency amplitude, and the low frequency amplitude.

The invention in at least one embodiment includes a system including at least two electrodes, and alertness means for providing a representation as to the alertness level of an individual based on EEG signals provided by the at least two electrodes when connected to the individual.

The invention in at least one embodiment includes a system for providing an index for an individual using at least one EEG signal, the system includes a Discrete Fourier transformer; a low frequency path connected to an output of the Discrete Fourier transformer, the low frequency path having a low bandpass filter covering the low frequency band, and a low frequency summation device connected to the low bandpass filter; a high frequency path connected to an output of the Discrete Fourier transformer, the high frequency path having a high bandpass filter covering the high frequency band, and a high frequency summation device connected to the high bandpass filter; and a divider connect to the low frequency summation device and the high frequency summation device, the divider outputs a ratio of the output of the high frequency summation device to the output of the low frequency summation device.

The invention in at least one embodiment includes a method for determining an index representative of the level of alertness/drowsiness of an individual including receiving an EEG signal, transforming the EEG signal into the frequency domain, summing all of the amplitudes for each frequency band, determining a total amplitude for all frequency bands, determining the ratio of each frequency band to the total amplitude for at least the lowest and highest frequency band, determining the index of the highest frequency band ratio to the lowest frequency band ratio, and providing the index.

IV. BRIEF DESCRIPTION OF THE DRAWINGS

V. DETAILED DESCRIPTION OF THE DRAWINGS

The invention includes a method for determining an index that is indicative of whether the person that is being monitored is likely able to perform a cognitive processing task. The method described in this example embodiment receives EEG signals for processing and determination of an index. The index is applicable to different individuals at least in part to individuals generating the same patterned brain waves in the different states of awake, drowsy, asleep, or active cognition.

An example of a system for use with the method obtains EEG signals recorded from scalp electrodes located at the C3 and C4 positions. The electrodes, for example, may be affixed to the individual or located in a head covering such as a hat or helmet. The recording system at a minimum must be able to acquire the EEG signals at a sampling rate of at least 1000 Hz, i.e., 1000 samples per second. There are a variety of commercial polygraph systems available that can provide this minimal sampling period, for example, Grass/Telefactor Gamma® Systems. Depending upon the implementation, the electrodes are directly connected to the stationary polygraph system, a processing system (e.g., FIG. 16) or to a portable personal data assistant (PDA) specifically equipped with electronic capability for acquiring and processing the EEG signals. In at least one other example of a system embodiment, the electrodes are in wireless communication with at least one other aspect of the system. The EEG signals may be processed in real-time taking into account a moving sampling window or stored for later analysis. In at least one other example of a system embodiment, the results of the analyzed EEG signals are transmitted to a central monitoring station for use by a supervisor or a commander. In at least one other example of a system embodiment, the raw (or digitally converted) EEG signals are transmitted to a central monitoring station for analysis by a supervisor or a commander.

Figure 1:
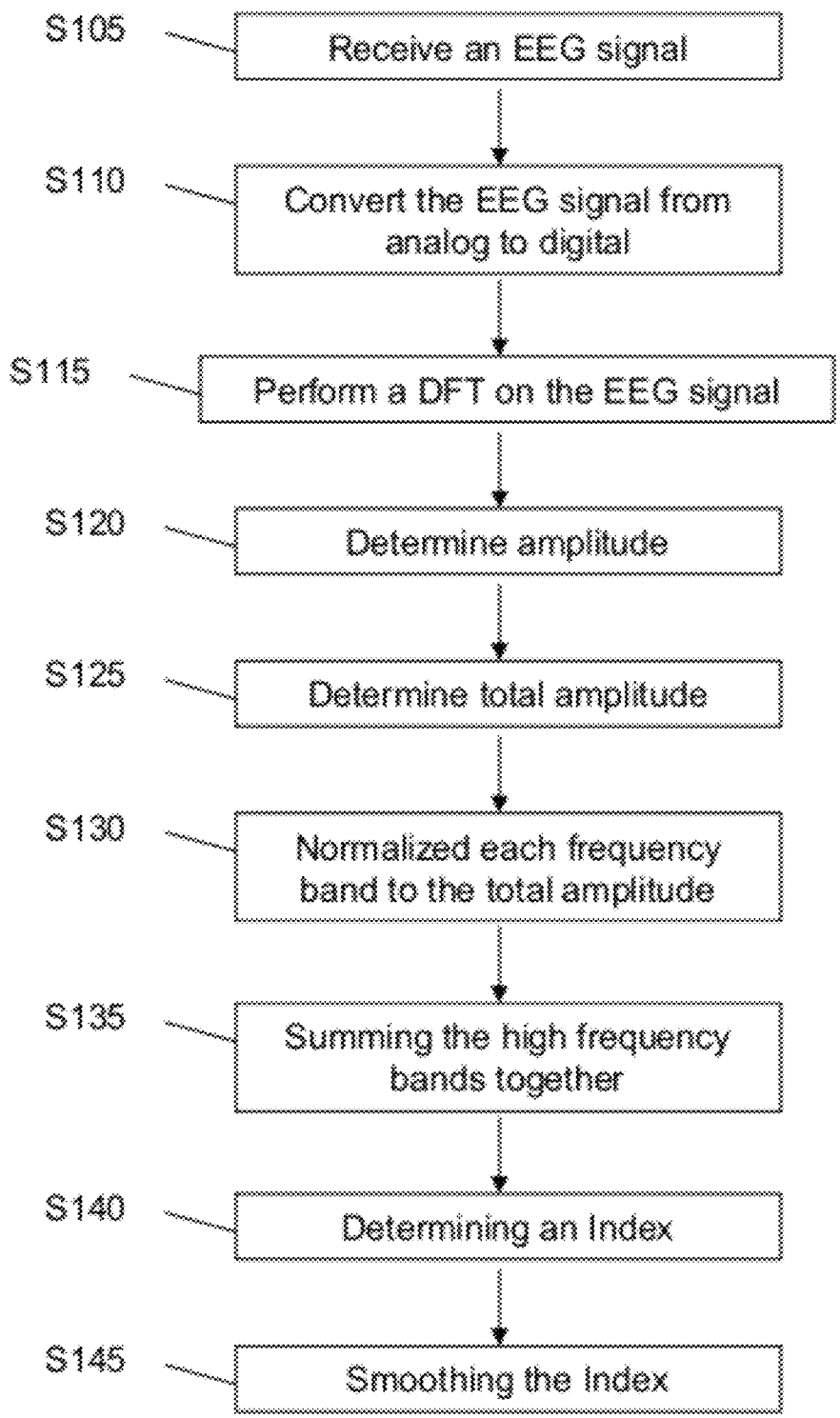
FIG. 1 illustrates a method according to at least one embodiment of the invention.
Figure 2:
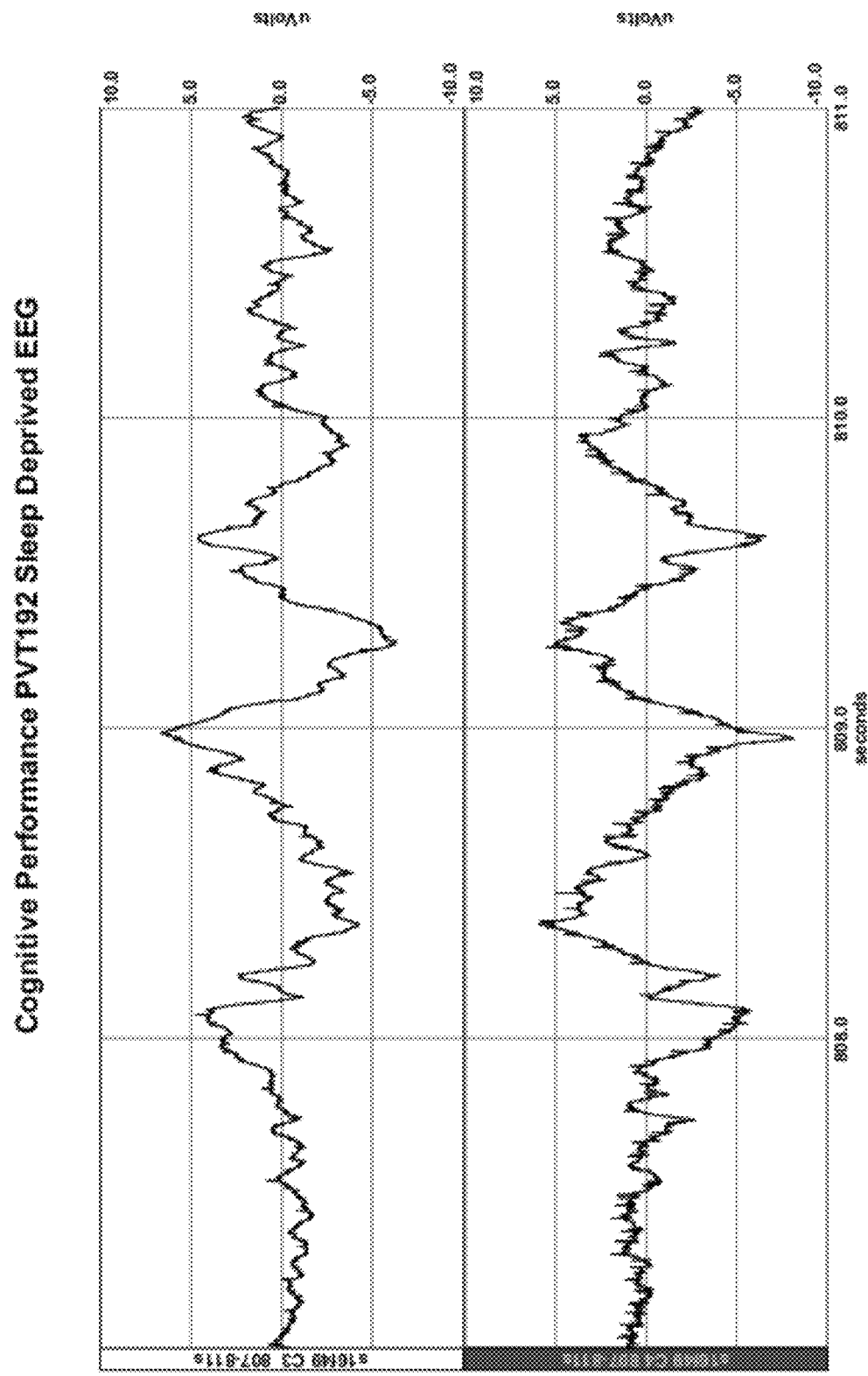
FIG. 2 illustrates raw EEG data.

An example of a method according to the invention is illustrated in FIG. 1. The method receives at least one EEG signal as an input, S105. FIG. 2 illustrates a sleep deprived EEG signals from C3 and C4. The EEG signal is converted from an analog signal to a digital signal, S110. If the EEG signal is digital as outputted by the electrodes, then step S110 can be omitted. Based on this disclosure, these two steps could be performed separate from the rest of the method including by different equipment or system.

The digitized sample is a representation of the EEG signal in the time domain. The method transforms the digitized sample to the frequency domain by discrete Fourier Transform (DFT) on a second-by-second basis, S115, although different epoch lengths can be utilized depending upon the desired resolution of data desired. Furthermore, the epoch length is not restricted and the user may select any length suitable for his/her use. However, the DFT result applies to the entire epoch then, i.e., 30 seconds as in polysomnography, and no specific incident of alertness/drowsiness/sleepiness can be pin-pointed within that epoch. Second-by-second is believed to be the smallest discrete increment allowing a resolution capable of showing instantaneous changes—what some sleep researchers call "microsleep", a moment when there is a lapse in cognitive capability possibly allowing a catastrophic event to occur. The output of the DFT is 500 frequency components from 1 Hz to 500 Hz representative of power ($\mu V^2$). The amplitude ($\mu V$) of each frequency component is obtained by taking the square root of power, S120, which provides a linear and therefore additive property. The Total Amplitude (TA) per second is obtained by summing all of the amplitudes of frequencies in the range of 1 to 500 Hz, S125. In at least one embodiment, the frequencies are separated into seven frequency bands as follows:

1. 1-15 Hz
2. 16-50 Hz
3. 51-100 Hz
4. 101-200 Hz
5. 201-300 Hz
6. 301-400 Hz
7. 401-500 Hz

Alternatively, the first two frequency bands may be 1-20 Hz and 21-50 Hz, respectively. The difference between these range sets is that 1-20 Hz provides a more certain determination of drowsiness, while 1-15 Hz has a natural bias towards sleepiness. Each of these frequency bands at their lowest level provides about 5% of the Total Amplitude (TA). The 0 Hz frequency is omitted because it would bias the power spectrum towards the lower frequency band. Typically, if the lower frequency band is more than 50% of the Total Amplitude (TA), then the individual is asleep. Alternatively, the bands 5-7 could be combined into one band of 201-500 Hz, and if this occurs then the summation step S135 is omitted.

Figure 3:
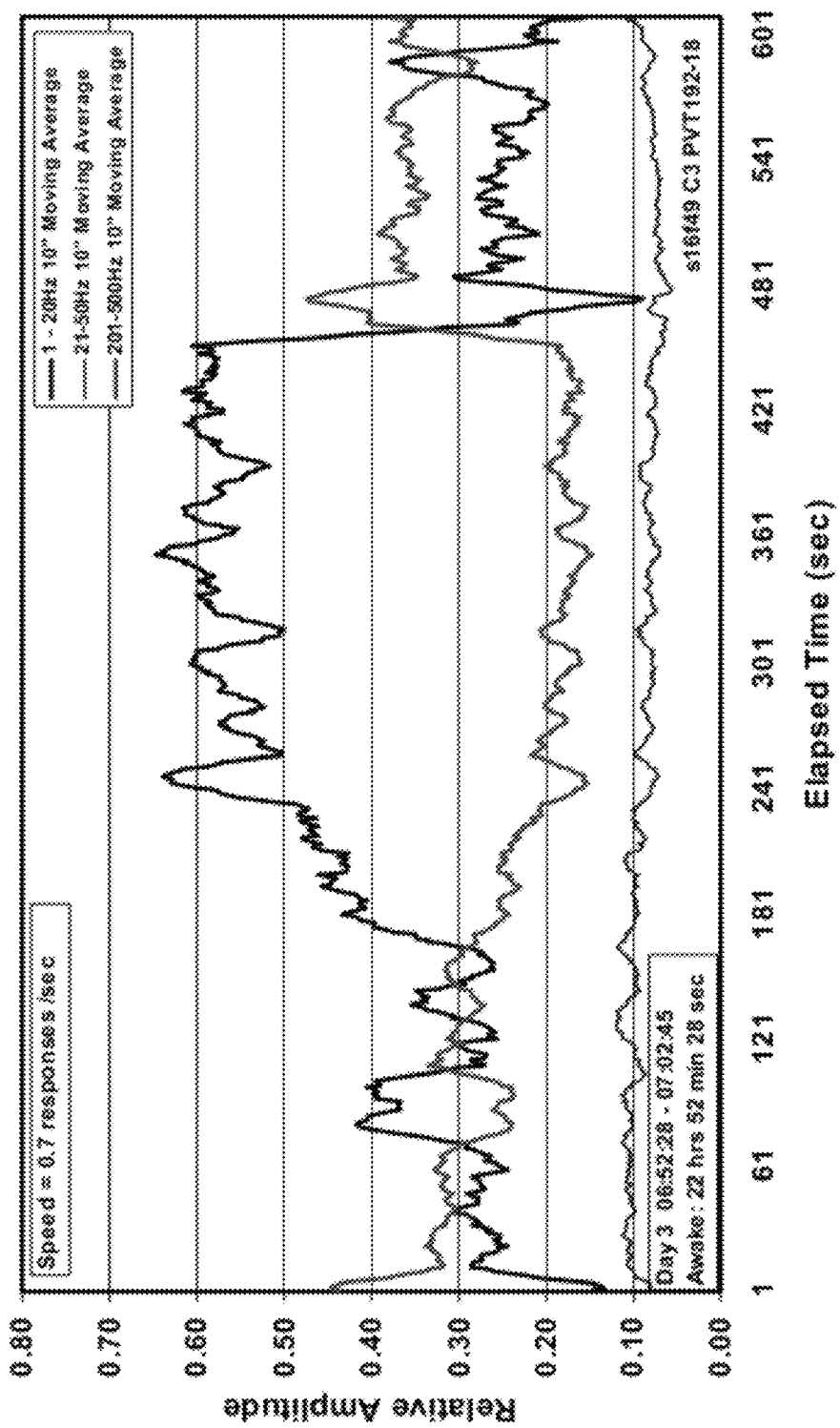
FIG. 3 illustrates the EEG data from FIG. 2 broken into frequency bands and normalized.

The sums of each frequency band's amplitudes are calculated and normalized with respect to the Total Amplitude (TA), S130. FIG. 3 illustrates the normalized amplitudes for the EEG signals illustrated in FIG. 2 using a ten second moving average to smooth the data, which the use of a moving average is discussed in a later embodiment. This provides the relative contribution of each frequency band to total energy in each second and allows for intra-individual as well as inter-individual comparisons regardless of the absolute amplitude values which may vary within as well as across individuals depending on the scalp-electrode contact and individual impedance. The frequency bands in the range of 201-500 Hz are summed together to form a single frequency band, S135. One of ordinary skill in the art will appreciate that other frequencies can be included in this single frequency band. The higher frequency band (201-500 Hz) is indicative of brain activity during active cognitive processing in individuals.

Figure 4:
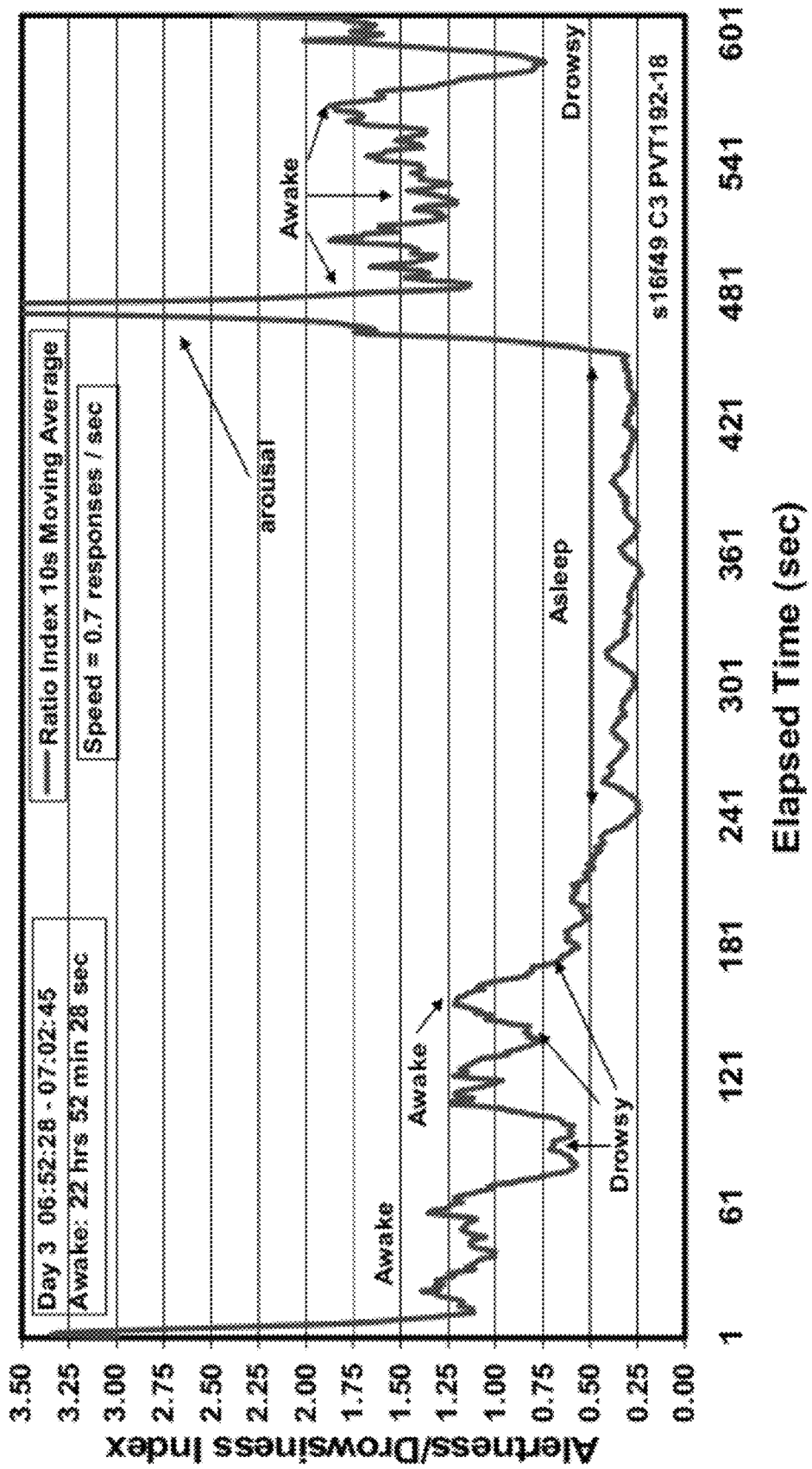
FIGS. 4-13 illustrate graphs depicting the index value and its changes in particular between sleep deprived and non-sleep deprived states. The index value is a continuous quantity, but for ease of illustration is expressed in intervals of 0.25 along the Y-axis of these graphs.

The index value is determined based on the ratio of the proportion of high frequency band (201-500 Hz) to proportion of low frequency band (either 1-15 Hz or 1-20 Hz) contribution to the Total Amplitude (TA), S140. FIG. 4 illustrates the Index for the normalized EEG readings from FIG. 3. The ratio can use the raw Total Amplitude (TA) or the normalized Total Amplitude (TA). In embodiments where the raw Total Amplitude (TA) is used from S125, then the normalization step S130 may be omitted. The index value as determined reflects the intrinsic nature of the constantly oscillating state of energy in the brain, i.e., not a steady state but rather one having potentially large relative value changes from one second to the next.

In at least one other example of a method according to the invention, the method further includes smoothing the string of index values forming the data with a moving average, S145. An example of a moving average is 10 point, i.e., 10 second window. The moving average parameter can be any reasonable value depending upon the resolution desired including values falling within the range of 2 to 60 seconds. Further example values include 5 seconds, 20 seconds, and 30 seconds. The moving average will provide greater stability for the index value as well as providing more easily viewed data.

The moving average alternatively may instead be used in connection with each frequency band as illustrated, for example, in FIG. 3.

In general, an Index greater than or equal to 1.25 (to as high as 3.5) signifies awake, alert and capable of cognitive processing. An Index around 1.0 can be indicative of an alert state or a drowsy state depending upon the individual. An Index below 0.8 (or 0.9) is evident of a drowsy state and the asleep state is defined as the Index less than or equal to 0.25.

Figure 5:
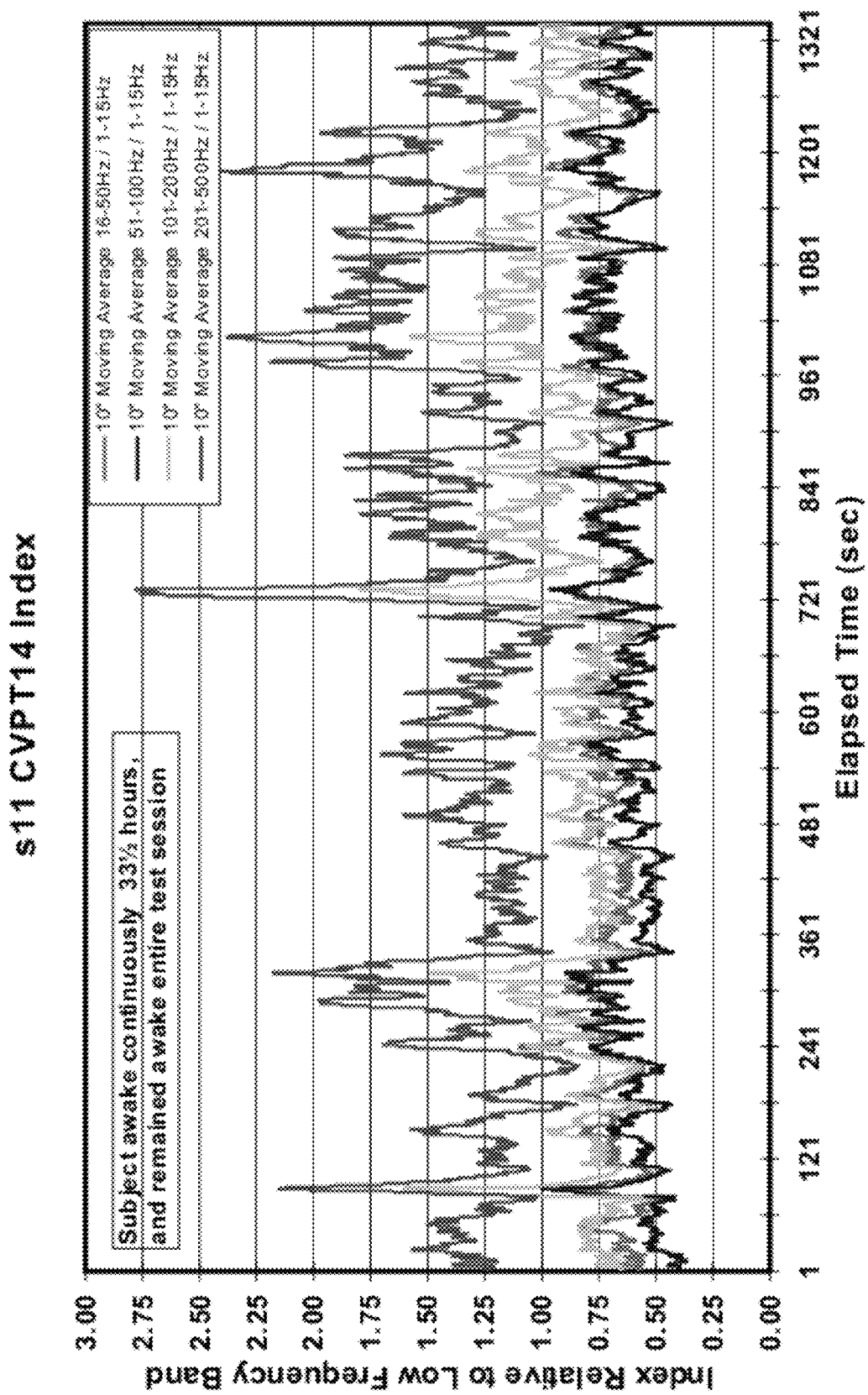
Figure 6:
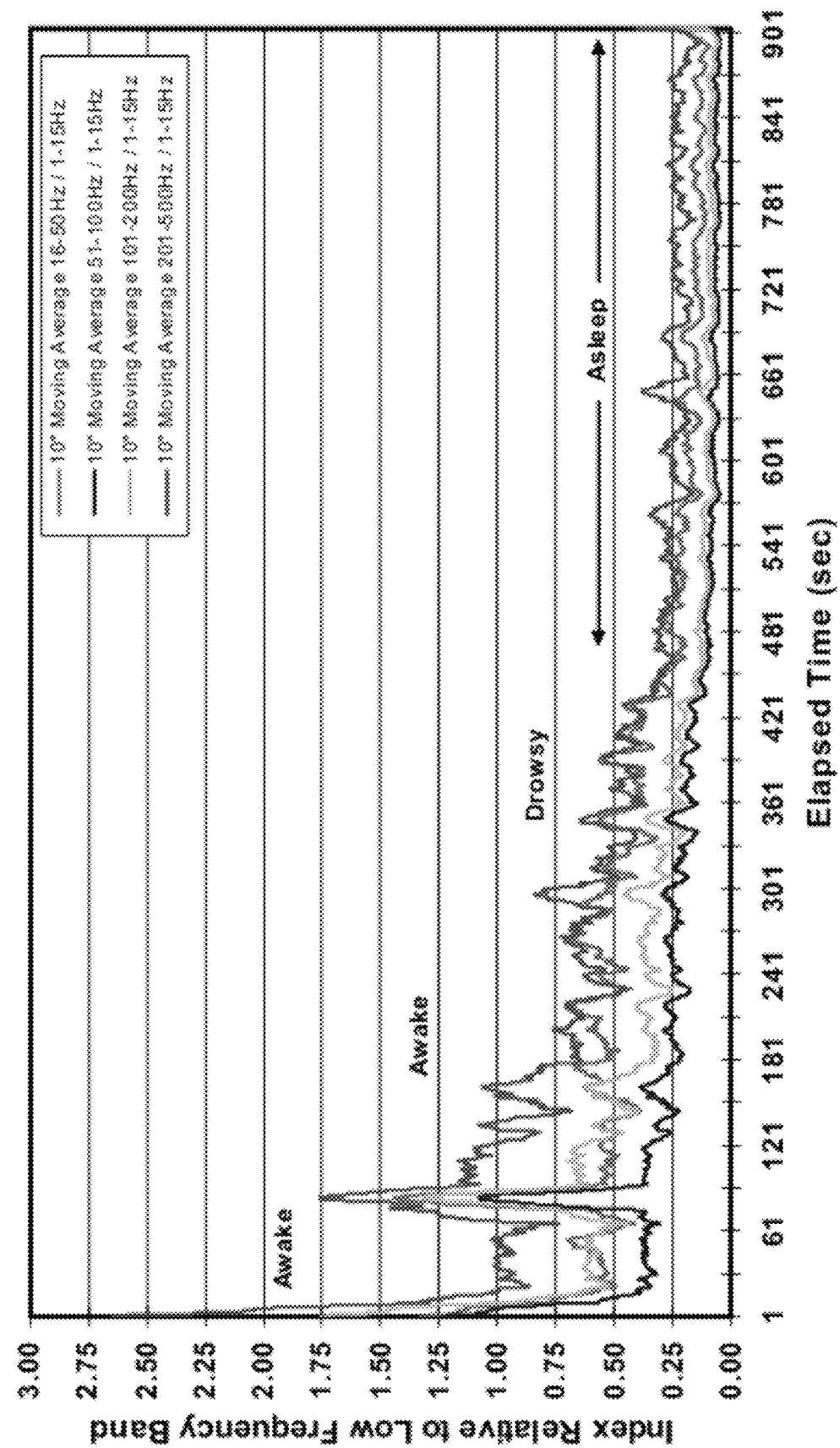

FIGS. 5 and 6 illustrate different Index calculations where the frequency range being compared to the lowest frequency range is different. The sensitivity for discriminating between different states is highest for the high frequencies of the 201-500 Hz range when compared to the 1-15 Hz range. FIG. 6 further illustrates the different states labeled between awake, drowsy, and asleep.

FIGS. 4 and 7-13 illustrate graphs depicting the index value and its changes in particular between sleep deprived and non-sleep deprived states. Although the Index is a continuous quantity, the Y-axis of these figures includes hash marks at intervals of 0.25. The Y-axis is not at the same scale for each of the illustrated graphs in order to better show each range difference at an appropriate resolution.

Figure 7:
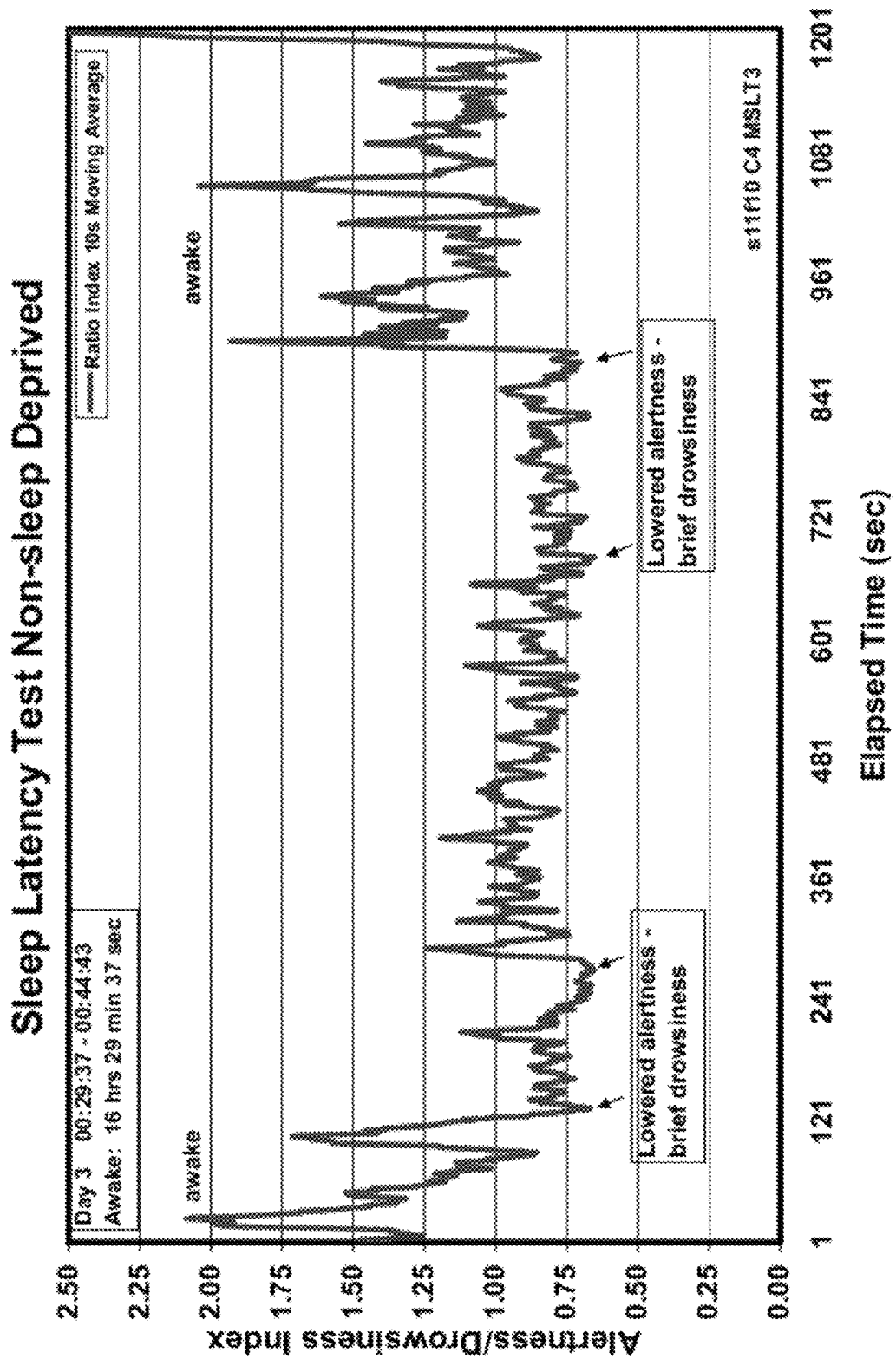
Figure 8:
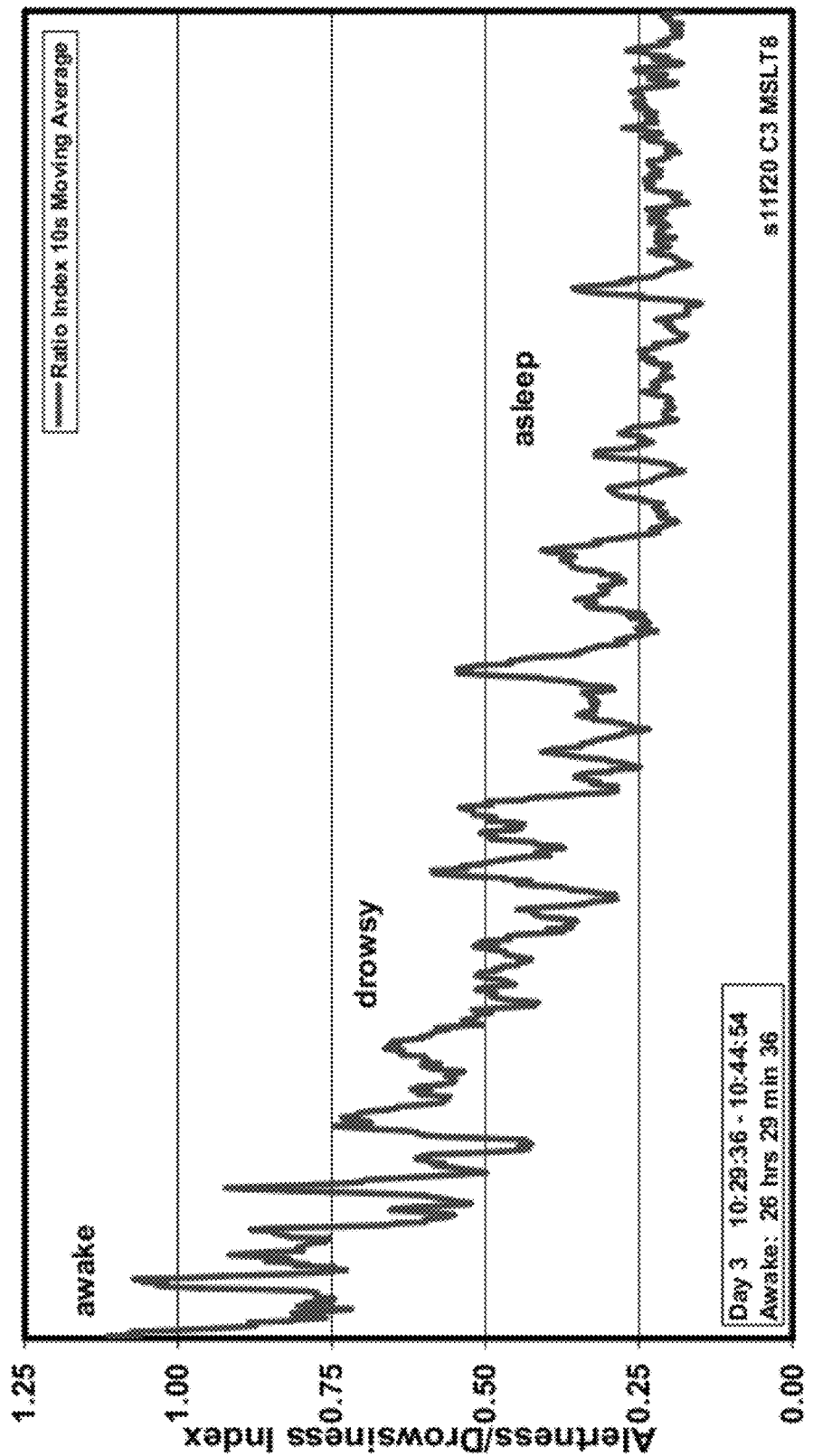

FIGS. 7 and 8 illustrate the Index during a sleep latency test in which the individual attempts to sleep within either a 20 minute or 15 minute period. FIG. 7 illustrates a sleep latency test of a non-sleep deprived individual who for the most part maintains the Index above 0.75, which is indicative of an awake state with slight drowsiness, except for two brief intervals when the Index declines slightly below this level. FIG. 8 illustrates a sleep latency test of a sleep deprived individual who exhibits a progressively declining Index as the subject proceeds from the awake state to the asleep state.

Figure 9:
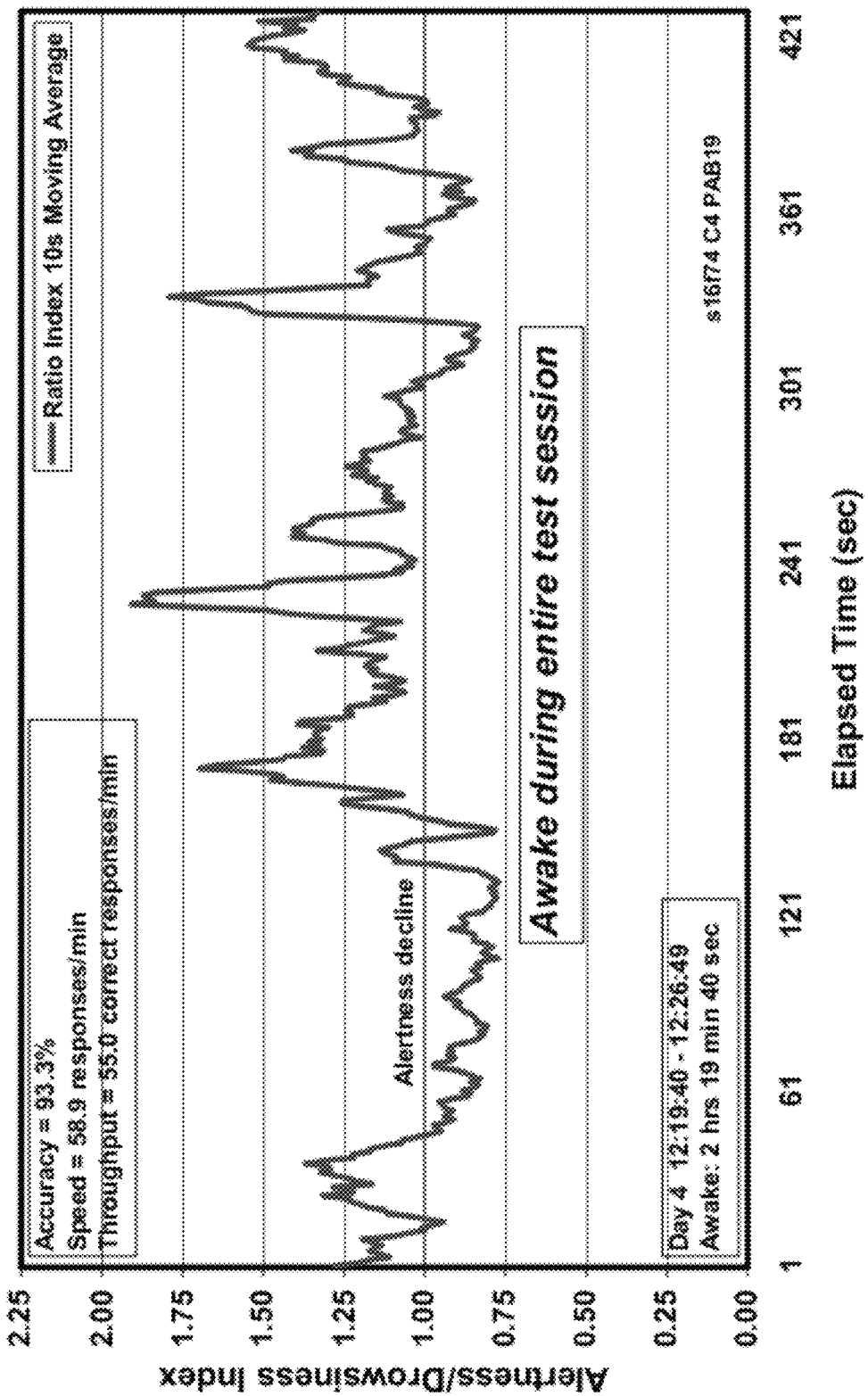
Figure 10:
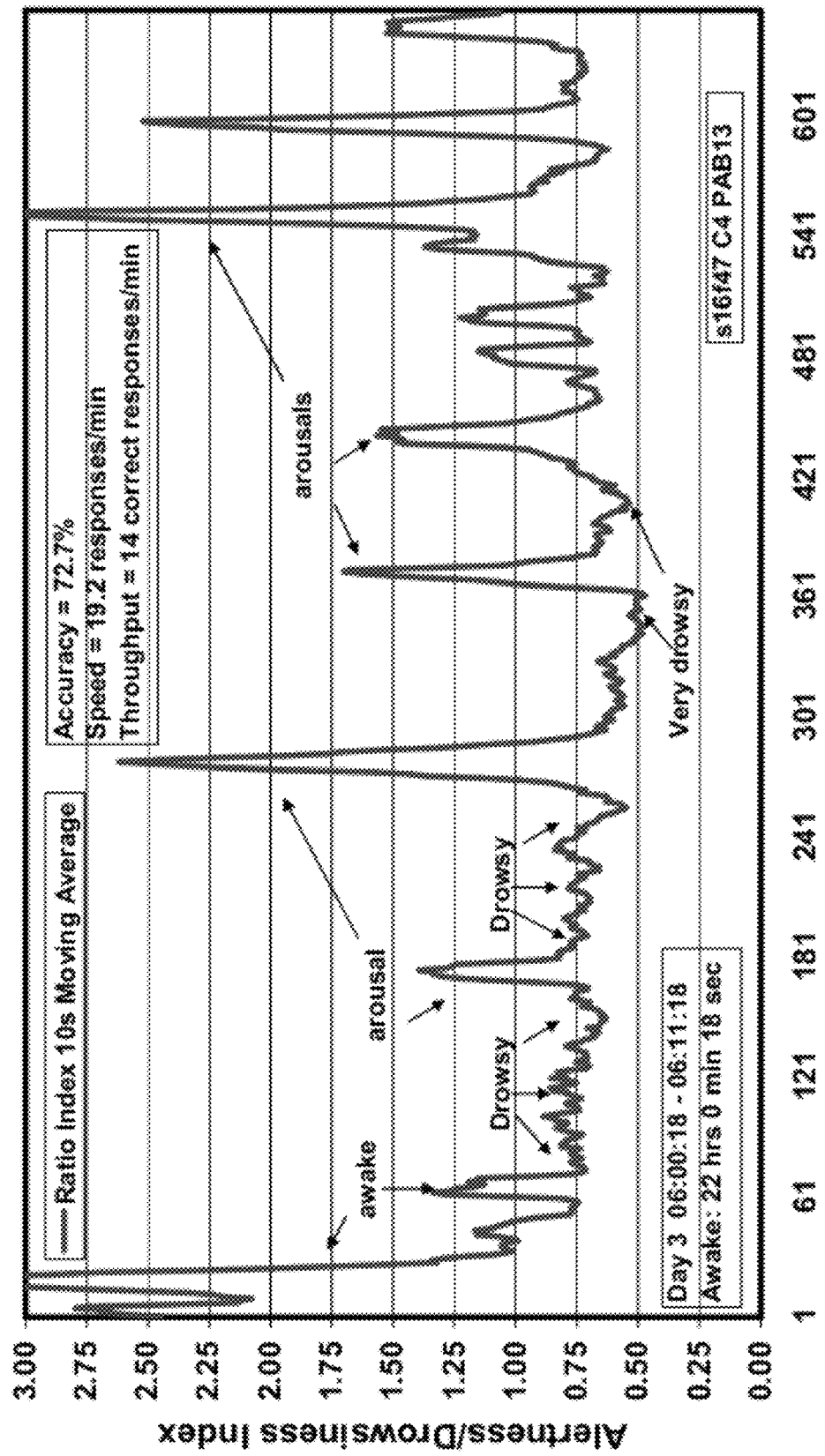

FIGS. 9 and 10 illustrate the Index for two individuals during a Performance Assessment Battery (PAB), which involves multiple types of cognitive processing, i.e., arithmetic, choice reaction time, memory, spatial orientation. FIG. 9 illustrates a PAB of a rested individual who except for a small period of slight alertness decline remains awake during the entire test session while maintaining a high level of throughput (i.e., the product of speed and accuracy) during the test session. The majority of the Index values are well above 1.0, and some extend to almost 2.0. FIG. 10 illustrates a PAB of a sleep deprived individual that shows a vastly different picture of the Index during PAB testing than that shown in FIG. 9. In FIG. 10, the individual is struggling to maintain alert wakefulness by repeated attempts of arousal from on-going drowsiness. Each arousal effort is not sustained for very long.

Figure 11:
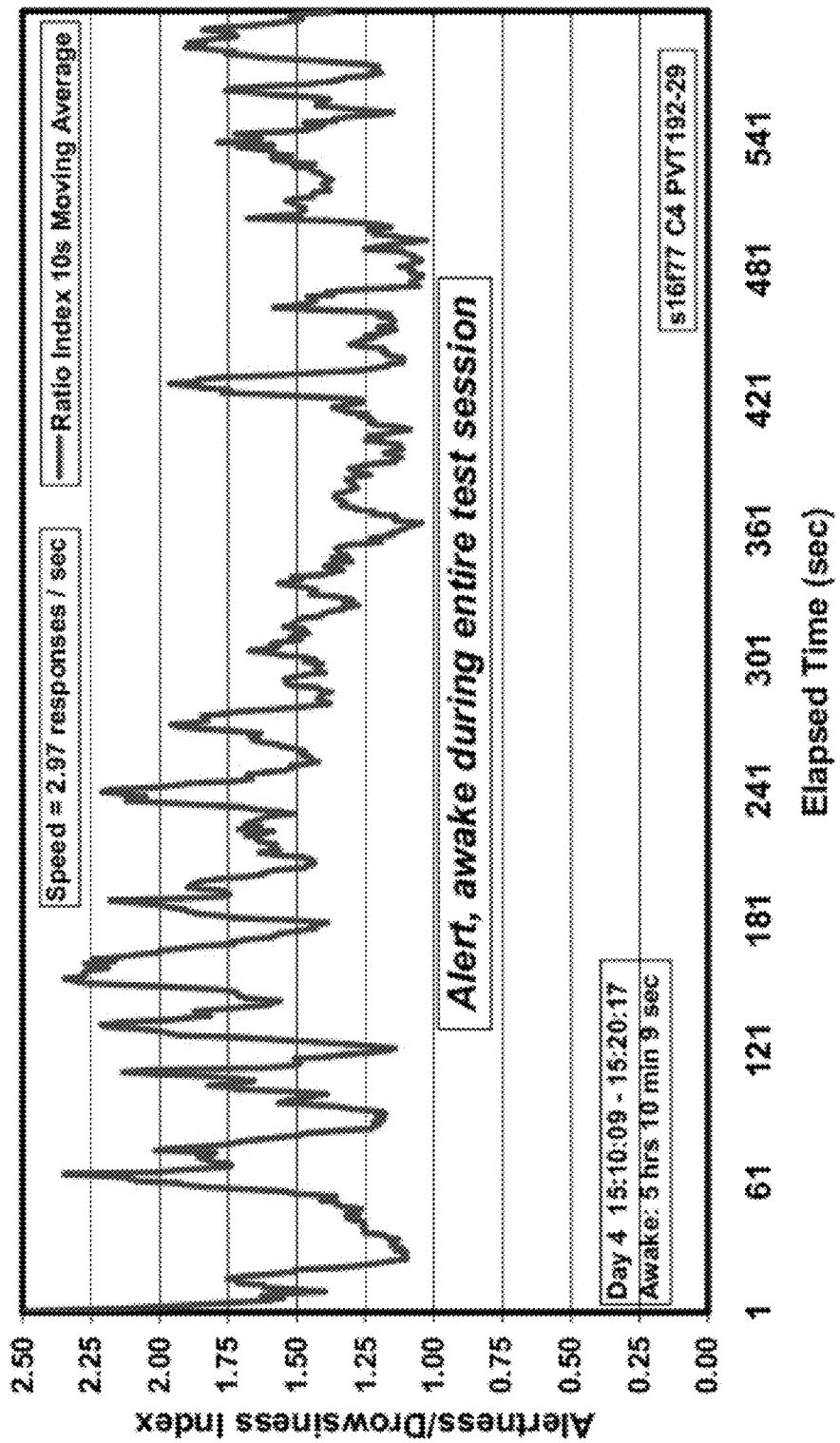

FIGS. 4 and 11 illustrate the Index during performance of a Psychomotor Vigilance Test (PVT), a task which requires sustained visual attention and vigilance. FIG. 11 illustrates a PVT of a rested individual who consistently has an Index greater than 1.0, which indicates the individual is awake and alert during the entire test session. On the other hand, FIG. 4 illustrates a PVT of a sleep deprived individual whose Index reflects the inability to maintain wakefulness during the test, in fact, the individual fell asleep for at least three continuous minutes at about four minutes into the test.

Figure 12:
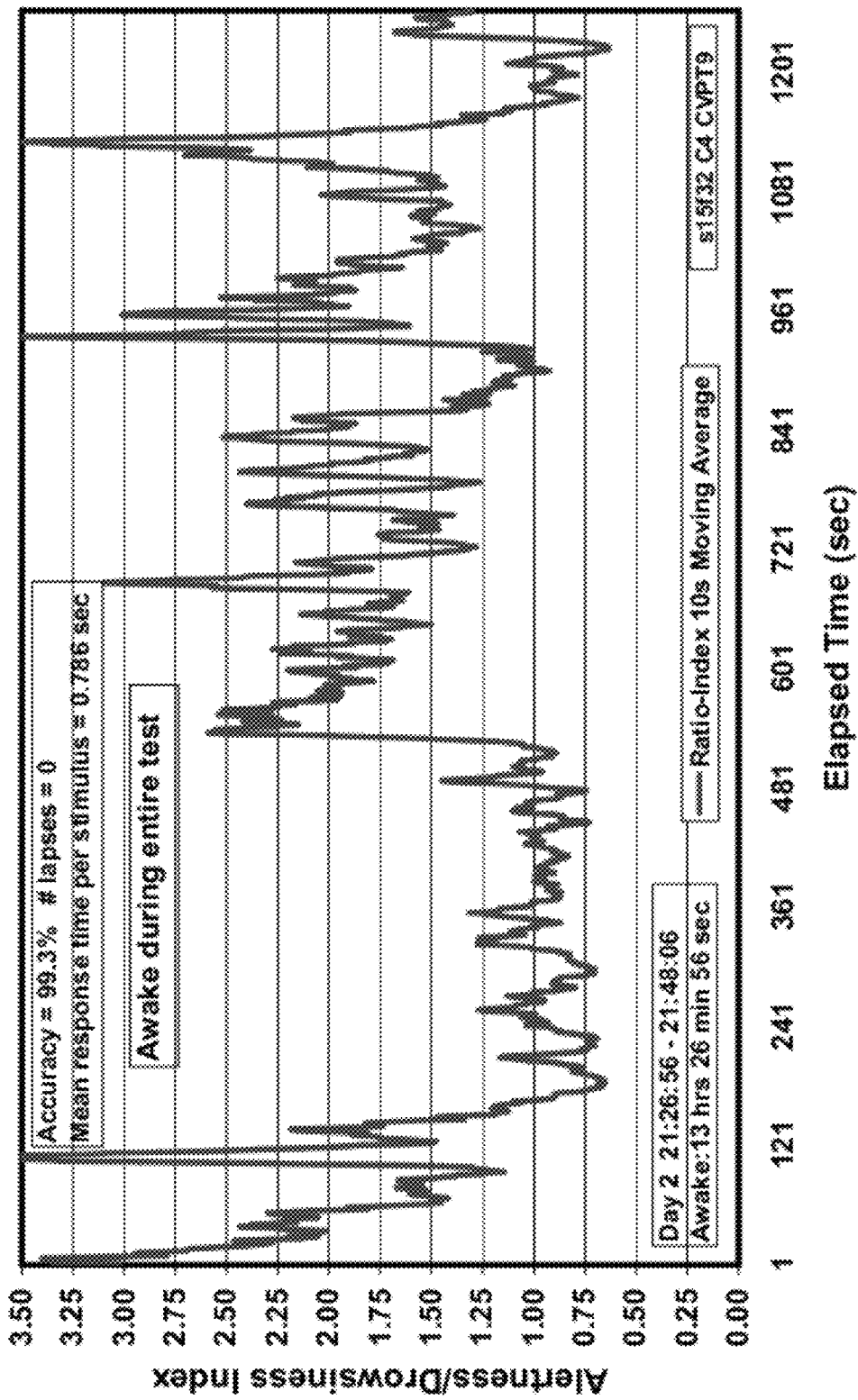
Figure 13:
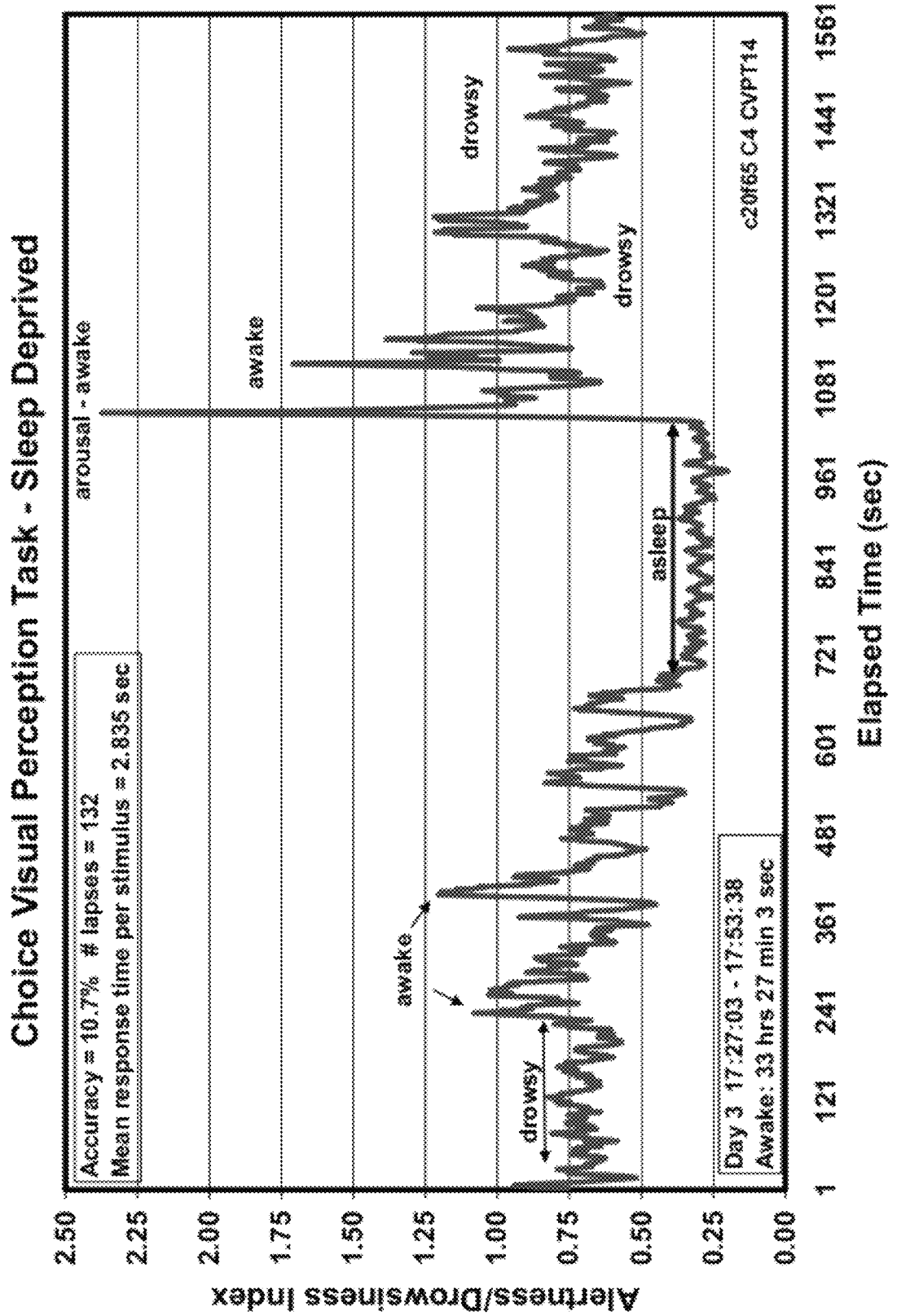

FIGS. 12 and 13 illustrate the Index during a Choice Visual Perception Test, which was the longest lasting test administered during the study from which this data was taken. The Choice Visual Perception Test requires both sustained peripheral visual attention and a manual response indicating left or right location to presence of single or double LED light stimuli of 250 milliseconds duration. The device used in this test was the patented Lateral Visual Field Tester (LVFT) invented by COL Michael Russo (U.S. Pat. No. 6,849,050).

FIG. 12 illustrates the test of a rested individual who maintained Index values (in excess of 0.75 and most of the time in excess of 1.0) reflecting the subject's rested state of being awake and alert during the entire test session as reflected by the high accuracy score and no lapses in responses. FIG. 13 illustrates a sleep deprived test session where the Index remained mostly at the level of drowsiness or had a progression towards drowsiness ending in an interval of at least four minutes in which the subject was asleep during the test session. The accuracy score and response lapses in 132 out of 150 stimuli clearly reflect that the individual was in an advanced state of drowsiness/sleep during the entire test session.

In another method embodiment according to the invention, the method provides assessment information regarding the state of the individual. A method for providing this information uses regression analysis of the 10 point moving average to obtain the slope value. Depending upon the point value, the regression analysis would use the same number of points. The slope provides a measure of the current status of the individual with reference to the immediate past 10 seconds in this example. If the value of the slope is positive, then alertness is trending upwards. If the value of the slope is negative, then alertness is trending downwards. If the value of the slope is zero, there is no change from the previous 10 seconds in this example. If the value of the slope is near zero and positive, there is a potential state change from drowsiness towards alertness. If the value of the slope is near zero and negative, there is a potential state change from alertness towards drowsiness.

In another method embodiment according to the invention, the method adds a filtering step between S110 and S115 of FIG. 1 to filter out the line frequency and its harmonics (60, 120, 180, 240, 300, 360, 420, 480 Hz). An example of a way to accomplish a filter is with a narrow band FIR filter to eliminate the raw EEG data for these frequencies. In a further example embodiment, the average of the 1000 EEG values in each second is obtained and subtracted from each of the 1000 EEG values as the average is the DC or zero frequency. The decision to use a filter can be based on a visual inspection of an EEG waveform.

In the instrument used in the study, 60 Hz noise was a prominent artifact. In instruments not affected by line frequency interference, filtering or not filtering would be an option. Filtering out these few frequencies does not affect the overall relationship in the Index, in particular because the amplitude in the higher frequency bands is a magnitude of order lower than the low frequency bands, so large numbers are not deleted. The highest magnitude is the 60 Hz artifact, but the Index is not impacted by this frequency.

In another method embodiment according to the invention, the method eliminates a sample in which the Total Amplitude (TA) of the entire spectrum, for example, 1 to 500 Hz although other ranges could be utilized, exceeds the mean TA by 3 standard deviations (mean TA+3 sd). In some embodiments, the threshold is met if the current Total Amplitude exceeds the mean TA by 2 standard deviations (mean TA+2 sd). An example of a way to obtain the mean TA is for each subject is to record an initial 60 second sample baseline EEG under normal conditions where the individual is well rested (i.e., not sleep deprived), awake and sitting quietly. The average and standard deviation of the sixty Total Amplitudes are calculated. This provides assurance that true high amplitudes are not rejected. This is done to take into account that each subject differs in absolute values for the EEG measurements, due to differences in individual impedances, electrode adherence, etc. This will eliminate EEG readings that are considered to be artifactual, and as such the relative magnitudes can be adjusted.

In another method embodiment according to the invention, the method adds providing a notification regarding the Index value. The notification can be to the individual being monitored, to a supervisor, to a monitoring system or other data collection system. In at least one example of a system embodiment according to the invention, the system provides a notification once the Index crosses a certain threshold and/or the slope of the Index is indicating the individual is approaching drowsiness or sleep. The threshold depending upon the implementation can be at 1.0, 0.8, 0.5 or at some level above these to provide the individual a chance to stop the task being performed or to take other action to reduce the risk of an incident or other problem.

Figure 14:
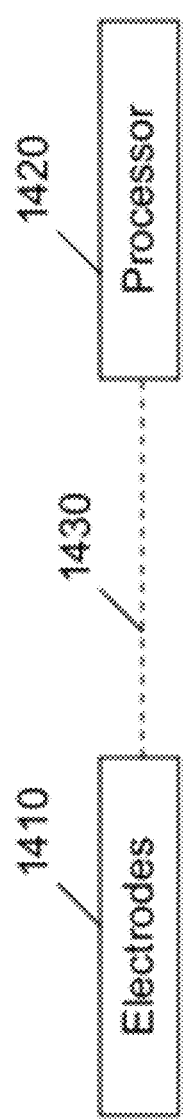
FIG. 14 illustrates a system according to at least one embodiment of the invention.
Figure 15:
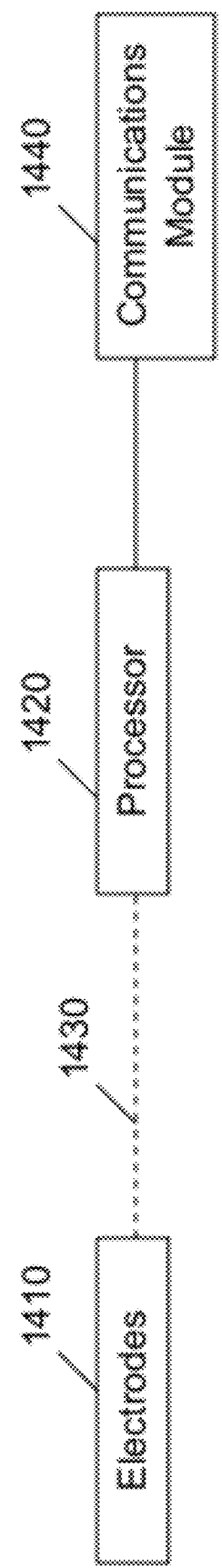
FIG. 15 illustrates a system according to at least one embodiment of the invention.

An example of a system for performing the above described methods is illustrated in FIG. 14. The system includes at least two electrodes 1410 in communication with a processor 1420. The processor includes alertness means for providing a representation as to the alertness level of an individual based on EEG signals provided by said at least two electrodes when connected to the individual. The communication between these components can be accomplished wirelessly if the electrodes include or are connected to transmitters for communicating with the processor or these components can be wired together as such the dash line 1430 represents these possibilities as a means for communicating EEG signals from said at least two electrodes to the alertness means. In at least one example of a system embodiment illustrated in FIG. 15, the system further includes a communications module 1440 for sending notifications. The communications module 1440 can include a transmitter or other output for sending a signal to alert the individual, their supervisor, or another system.

Figure 16:
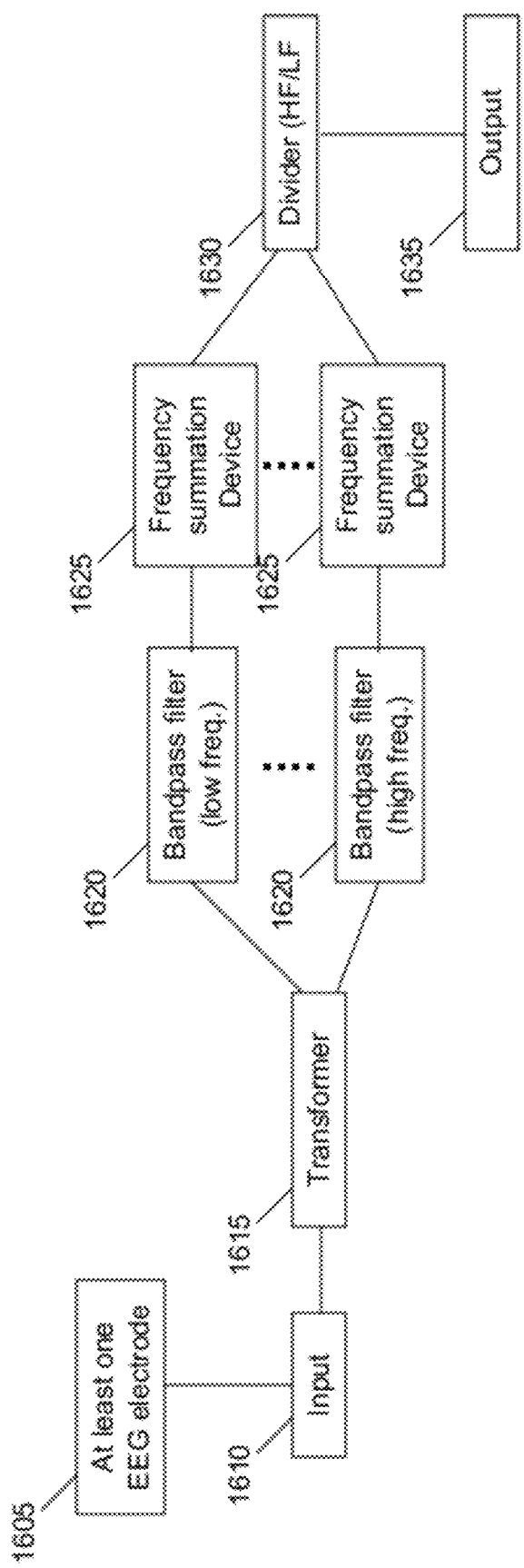
FIG. 16 illustrates a system according to at least one embodiment of the invention.

FIG. 16 illustrates a further example of a system embodiment according to the invention. An input signal is obtained from at least one EEG electrode 1605 that is connected to an input (or receiver) 1610. A transformer 1615 receives the input signal and transforms the input signal from the time domain to the frequency domain, for example, using a Discrete Fourier Transform. After the signal is converted into the frequency domain, the signal is branched into at least two paths for processing the signal a low frequency range and a high frequency range. In each path, the frequency signal is passed through a bandpass filter 1620 to eliminate extraneous frequencies outside of the desired frequency range. The filtered signals each enter a respective frequency summation device (or summation means) 1625 that adds all of the amplitudes for each frequency in the frequency range that provides as an output the amplitude for the frequency range. Another example of the frequency summation device is to integrate the frequency data over the respective frequency ranges. The at least two paths come together to provide inputs into a divider 1630 that divides the high frequency range amplitude by the low frequency range amplitude to produce an index representing the alertness/drowsiness of the individual wearing the at least one EEG electrode. Examples of where the output 1635 for the divider 1630 may go include memory, a data file, a display, an electronic signal, a transmitter for sending to another device wirelessly, and any combination of these examples.

In addition to the components discussed in FIG. 16, the system in other embodiments includes at least one amplifier to increase the signal strength for processing, an analog-to-digital convertor as part of or after the input, and a threshold detector connected to an alarm to notify the individual and/or another entity when the individual becomes drowsy. A further embodiment includes individual pathways for a plurality of frequency bands to allow calculation of a total amplitude for all frequencies to provide a check that the low and high frequency ranges do not exceed predetermined percentage thresholds that would indicate that a validity issue exists for that sampling period. Examples of frequency bands are provided above in connection with the above-described method embodiments.

In a study that included thirteen subjects who underwent a four day study which included a period of forty hours of continued wakefulness. This study provided data that was used in previously discussed FIGS. 2-13. The subjects wore EEG electrodes at two central locations, C3 and C4, for the test sessions for seven different cognitive tasks and two overnight sleep sessions. The cognitive tests ranged from five minutes to twenty-six minutes and included stimulus presentations that were directly synchronized with two tasks, the CVPT and the PAB. EEG records were collected and analyzed for each subject. The analysis of these EEG records in conjunction with the cognitive test data confirms the validity of the index.

This study included thirteen individuals having a mean age of $30.5 \pm 6.0$ yrs. The number of hours of sleep deprivation was 40. The physiological signals monitored included: EEG, EOG, EMG, EKG, Wrist and tri-axial Actigraphy, and pulse. The signal sampling rate was 1000 Hz for the EEG and EKG monitoring. Each participant was resident in a sleep laboratory for four days. The schedule was as follows:

Day 1: Electrodes were attached to the subjects. The subjects were trained on the test tasks and allowed eight hours in bed.

Days 2 & 3: Scheduled hourly testing of tasks using at least one of SLT, CVPT, PAB, and PVT over the next forty hours.

Day 4: The subjects were allowed recovery sleep of ten hours beginning at 0000 and awoken at 1000 to resume hourly testing till 1800. The subjects were then debriefed, electrodes removed, and departed the laboratory at 1900.

The study produced 326 EEG files for each subject and a total of 4,238 files, of which about 150 were not usable. Each subject received the following number of tests: 19 CVPT, 12 MSLT, 20 PAB, 60 PDA based PVT, 20 computer based PVT, 30 PVT, and 2 sleep.

The study results were that the sleep state suppresses all high frequency EEG activity; EEG signals in high frequency range are manifestations of active thought processes; sleep deprivation increases low frequency amplitude and decreases high frequency amplitude; a decline in alertness, or conversely, increase in drowsiness results in equivalent loss of cognitive function capacity to respond to external stimuli resulting in apparent "lapse". Without cognitive function capacity, there can be no cognitive performance. High frequency EEG provides an objective assessment for quantifying cognitive function capacity, can indicate when intervention measures may be introduced to alleviate a drowsy/sleepy state, and can be an aid in cognitive performance modeling.

The invention can take the form of an entirely hardware embodiment, an entirely software embodiment or an embodiment containing both hardware and software elements. In at least one embodiment, the invention is implemented as a circuit or an application specific integrated circuit (ASIC). In at least one embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

Examples of the medium include an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include compact disk—read only memory (CD-ROM), compact disk—read/write (CD-R/W), DVD, and Blu-ray.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Computer program code for carrying out operations of the present invention may be written in a variety of computer programming languages. The program code may be executed entirely on at least one computing device, as a stand-alone software package, or it may be executed partly on one computing device and partly on a remote computer. In the latter scenario, the remote computer may be connected directly to the one computing device via a LAN or a WAN (for example, Intranet), or the connection may be made indirectly through an external computer (for example, through the Internet, a secure network, a sneaker net, or some combination of these).

It will be understood that each block of the flowchart illustrations and block diagrams and combinations of those blocks can be implemented by computer program instructions including software and/or means. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowcharts or block diagrams.

The various embodiments described above may be combined in a variety of ways with each other. Furthermore, the steps and number of the various steps illustrated in the figures may be adjusted from that shown.

It should be noted that the present invention may, however, be embodied in many different forms and should not be construed as limited to the embodiments set forth herein; rather, the embodiments set forth herein are provided so that the disclosure will be thorough and complete, and will fully convey the scope of the invention to those skilled in the art. The accompanying drawings illustrate examples of embodiments of the invention.

Although the present invention has been described in terms of particular example and alternative embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the preferred and alternative embodiments described above can be configured without departing from the scope and spirit of the invention. Therefore, it is to be understood that, within the scope of the appended claims, the invention may be practiced other than as specifically described herein.

VI. Industrial Applicability

The invention can be utilized in a variety of settings to provide information as to whether an individual is becoming drowsy or has fallen asleep to avoid problems developing as a result. For example, an air traffic controller monitoring radar would receive notification along with a supervisor if the air traffic controller was becoming drowsy or fell asleep. Another example of an industry that would benefit from this invention is the trucking industry, because the driver may not be aware of their condition and this would provide a notification that they have become drowsy.

The invention can also be utilized as a research tool, for example, to see the impact of sleep schedules and/or pharmaceutical products and/or drugs on individuals. In these circumstances the invention may be coupled with cognitive tests to be performed by the individual.

I claim:

1. A method comprising:
  transforming a EEG signal to the frequency domain with a Discrete Fourier Transform using a processor,
  obtaining an amplitude of each frequency component using the processor,
  summing all of the amplitudes of frequencies in the range of 201-500 Hz to obtain a high frequency amplitude using the processor,
  summing all of the amplitudes of frequencies in the range of 1 to at least 15 Hz to obtain a low frequency amplitude using the processor, and
  calculating an Index based on a ratio of the high frequency amplitude to the low frequency amplitude using the processor.

2. The method according to claim 1, further comprising smoothing the Index using the processor.

3. The method according to claim 2, wherein smoothing the Index using a 10 point moving average.

4. The method according to claims 2, further comprising obtaining a slope value of the Index using the processor.

5. The method according to claim 1, wherein the low frequency amplitude is obtained for frequencies in the range of 1-20 Hz.

6. The method according to claim 1, further comprising:
  obtaining an EEG signal, and
  converting the EEG signal from analog to digital.

7. The method according to claims 6, further comprising smoothing the Index using a 10 point moving average using the processor.

8. The method according to claim 7, further comprising obtaining a slope value of the Index using the processor.

9. The method according to claim 1, further comprising summing all of the amplitudes of each frequency component to obtain a total amplitude using the processor.

10. The method according to claim 9, wherein obtaining the amplitude of each frequency component includes grouping the frequencies into frequency bands using the processor.

11. The method according to claim 10, wherein the frequency bands include 1-15 Hz, 16-50 Hz, 51-100 Hz, 101-200 Hz, 201-300 Hz, 301-400 Hz, and 401-500 Hz.

12. The method according to claim 10, wherein the frequency bands include 1-20 Hz, 21-50 Hz, 51-100 Hz, 101-200 Hz, 201-300 Hz, 301-400 Hz, and 401-500 Hz.

13. The method according to claim 10, wherein the frequency bands include 1-15 Hz, 16-50 Hz, 51-100 Hz, 101-200 Hz, and 201-500 Hz.

14. The method according to claim 1, wherein the amplitude of each frequency component is obtained by taking a square root of power for the respective frequency component.

15. The method according to claim 1, further comprising receiving the EEG signal from electrodes placed at the C3 and C4 locations.

16. The method according to claim 1, further comprising providing a notification when the Index is less than a threshold.

17. The method according to claim 16, wherein the threshold is equal to 1.

18. The method according to claim 16, wherein the threshold is equal to 0.8.

19. A method for determining an index representative of the level of alertness/drowsiness of an individual comprising:
 receiving an EEG signal from at least one electrode,
 transforming the EEG signal into the frequency domain using a processor,
 summing all of the amplitudes for each frequency band using the processor,
 determining a total amplitude for all frequency bands using the processor,
 determining the ratio of each frequency band to the total amplitude for at least the lowest and highest frequency band using the processor,
 determining the index of the highest frequency band ratio to the lowest frequency band ratio using the processor, and
 providing the index using the processor; and
 wherein the highest frequency band begins above 60 Hz and has an end point that is less than or equal to 500 Hz.

20. The method according to claim 19, further comprising eliminating any sample whose total amplitude exceeds a mean total amplitude plus 2 standard deviations using the processor,
 where mean total amplitude is calculated from an initial sampling period for the EEG.

21. The method according to claim 19, further comprising filtering out the power line frequency and its harmonics using at least one of the processor and at least one filter.

22. The method according to claim 19, wherein the highest frequency band is 201-500 Hz.

23. The method according to claim 19, wherein the lowest frequency band is 1-15 Hz.

24. The method according to claim 19, wherein the lowest frequency band is 1-20 Hz.

25. The method according to claim 19, wherein the amplitude of each frequency component is obtained by taking a square root of power for the respective frequency component.

26. The method according to claim 19, wherein at least one electrode includes one electrode placed at the C3 location and a second electrode placed at the C4 location.

27. A system comprising:
 means for transforming an EEG signal to the frequency domain with a Discrete Fourier Transform,
 means for obtaining the amplitude of each frequency component,
 means for summing all of the amplitudes of each frequency component to obtain a total amplitude,
 means for summing all of the amplitudes of frequencies in the range of 201-500 Hz to obtain a high frequency amplitude,
 means for summing all of the amplitudes of frequencies in the range of 1 to at least 15 Hz to obtain a low frequency amplitude, and
 means for calculating an Index based on the total amplitude, the high frequency amplitude, and the low frequency amplitude.

28. A system for providing an index for an individual using at least one EEG signal, said system comprising:
 a Discrete Fourier transformer;
 a low frequency path connected to an output of said Discrete Fourier transformer, said low frequency path includes
  a low bandpass filter covering the low frequency band, and
  a low frequency summation device connected to said low bandpass filter;
 a high frequency path connected to an output of said Discrete Fourier transformer, said high frequency path includes
  a high bandpass filter covering the high frequency band, and
  a high frequency summation device connected to said high bandpass filter; and
 a divider connect to said low frequency summation device and said high frequency summation device, said divider outputs a ratio of the output of said high frequency summation device to the output of said low frequency summation device.

* * * * *